United States Patent [19]

Townsend et al.

[11] Patent Number: 4,892,865

[45] Date of Patent: Jan. 9, 1990

[54] PYRROLO[2,3-D]PYRIMIDINE NUCLEOSIDES AS ANTIVIRAL AGENTS

[75] Inventors: Leroy B. Townsend; John C. Drach, both of Ann Arbor, Mich.; Steven H. Krawczyk, Bellerose, N.Y.

[73] Assignee: The Regents of the University of Michigan, Ann Arbor, Mich.

[21] Appl. No.: 127,487

[22] Filed: Dec. 1, 1987

[51] Int. Cl.$^4$ .......................... A61K 31/52; C07H 19/14
[52] U.S. Cl. ......................................... 514/43; 536/24; 536/26
[58] Field of Search ...................... 536/24, 26; 514/43, 514/45, 46

[56] References Cited

U.S. PATENT DOCUMENTS

3,817,982  6/1974  Verheyden et al. .
3,962,211  6/1976  Townsend et al. .
4,229,453  10/1980  Roth et al. .
4,596,798  6/1986  Shipman, Jr. et al. .

FOREIGN PATENT DOCUMENTS

3036390  5/1982  Fed. Rep. of Germany .

OTHER PUBLICATIONS

Bergstrom, D., et al., "Antiviral Activity of C-5 Substituted Tubercidin Analogues", *J. Med. Chem.*, 27:285-292 (1984).

Turk, S. R., et al., "Pyrrolo[2,3-d]Pyrimidine Nucleosides as Inhibitors of Human Cytomegalovirus", *Antimicrob. Agents Chemother.*, 31:544-550 (1987).

DeClercq, E., et al., "Antirhinovirus Activity of Purine Nucleoside Analogs", *Antimicrob. Agents Chemother.*, 29:482-484 (1986).

Shipman, C., Jr., "Antiviral Activity of Arabinosyladenine and Arabinosylhypoxanthine in Herpes Simplex Virus-Infected KB Cells: Selective Inhibition of Viral Deoxyribonucleic Acid Synthesis in Synchronized Suspension Cultures", *Antimicrob. Agents Chemother.*, 9:120-127 (1976).

Mitsuya, H., et al. "3'-Azido-3'deoxythymidine (BW A509U): An Antiviral Agent That Inhibits the Infectivity and Cytopathic Effect of Human T-Lymphtropic Virus Type III/Lymphadenopathy-Associated Virus In Vitro", PNAS (USA), 82:7096-7100 (1985).

Mitsuya, H., et al., "Inhibition of the In Vitro Infectivity and Cytopathic Effect of Human T-Lymphotrophic Virus Type III/Lymphadenopathy-Associated Virus (HTLV-III/LAV) by 2',3'-Dideoxynucleosides", PNAS (USA), 83:1911-1915 (1986).

Smith, C. M., et al., "Inhibitors of Hypoxanthine Metabolism in Ehrlich Ascites Tumor Cells in Vitro", *Cancer Treatment Reports*, 60:1567-1584 (1976).

Maruyama, T., et al., "Pyrrolopyrimidine Nucleosides. 18. Synthesis and Chemotherapeutic Activity of 4-Amino-7-(3-Deoxy-β-D-Ribofuranosyl)Pyrrolo[2,3-d]Pyrimidine-5-Carboxamide (3'-Deoxysangivamycin) and 4-Amino-7-(2-Deoxy-β-D-Ribofuranosyl)-Pyrrolo[2,3-d]Pyrimidine-5-Carboxamide ("-Deoxysangivamycin)", *J. Med. Chem.*, 26:25-29 (1983).

(List continued on next page.)

*Primary Examiner*—Ronald W. Griffin
*Assistant Examiner*—L. Eric Crane
*Attorney, Agent, or Firm*—Harness, Dickey & Pierce

[57] ABSTRACT

This invention relates to the use of certain substituted pyrrolo[2,3-d]-pyrimidine nucleosides in the treatment of viral infections, in particular those caused by human immunodeficiency virus type 1, herpes simplex virus type 1 and human cytomegalovirus. These substituted compounds retain antiviral properties present in their parent compounds yet exhibit significantly decreased levels of cytotoxicity.

17 Claims, 4 Drawing Sheets

OTHER PUBLICATIONS

DeClercq, E., et al., "Nucleic Acid Related Compounds. 51. Synthesis and Biological Properties of Sugar-Modified Analogues of the Nucleoside Antibiotics Tubercidin, Toyocamycin, Sangivamycin, and Formycin", *J. Med. Chem.*, 30:481–486 (1987).

Hansske, F., et al., "2' and 3'-Ketonucleosides and Their Arabino and Xylo Reduction Products", Tetrahedron 40:125–135 (1984).

Robins, M. J., et al., "A Mild Conversion of Vicinal Diols to Alkenes, Efficient Transformation of Ribonucleosides into 2'-ene and 2',3'-Dideoxynucleosides", *Tetrahedron Letters*, 25:367–370 (1984).

Jain, T. C. et al., "Reactions of 2-Acyloxyisobutyryl Halides with Nucleosides. III. Reactions of Tubercidin and Formycin", *J. Org. Chem.*, 38:3179–3186 (1973).

Tolman, R. L., et al., "Pyrrolopyrimidine Nucleosides. III. The Total Synthesis of Toyocamycin, Sangivamycin, Tubercidin, and Related Derivatives", *J. Am. Chem. Soc.*, 91:2102–2108 (1969).

Signas Chemical Co. Catalog, St. Louis, Mo., 1984, p. 898.

Robins, M. J., et al., Nucleic acid related compounds. 24. Transformation of tubercidin 2', 3'-O-orthoacetate into halo, deoxy, epoxide, and unsaturated sugar nucleosides 1, 211, Can. J. Chem., 55:1251–1259 (1977).

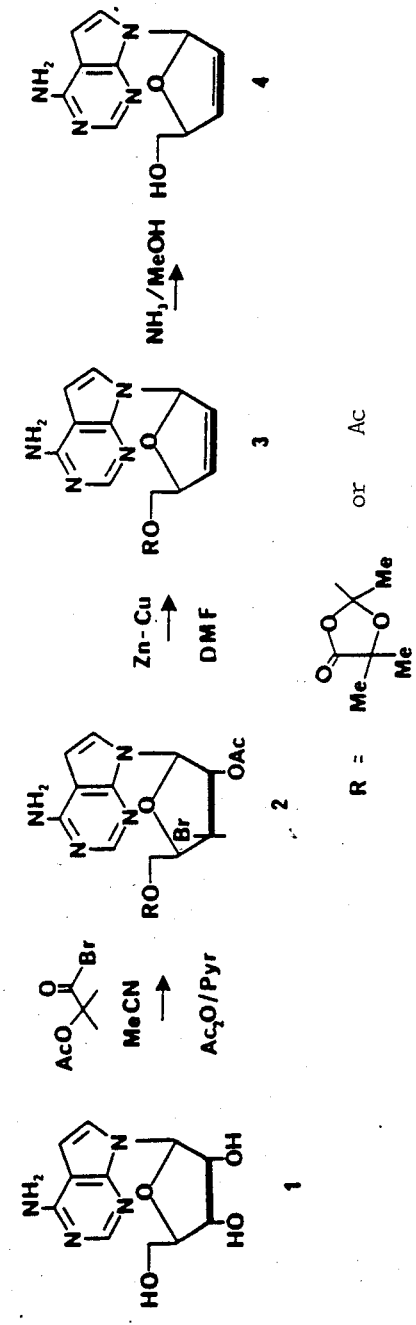
FIGURE I

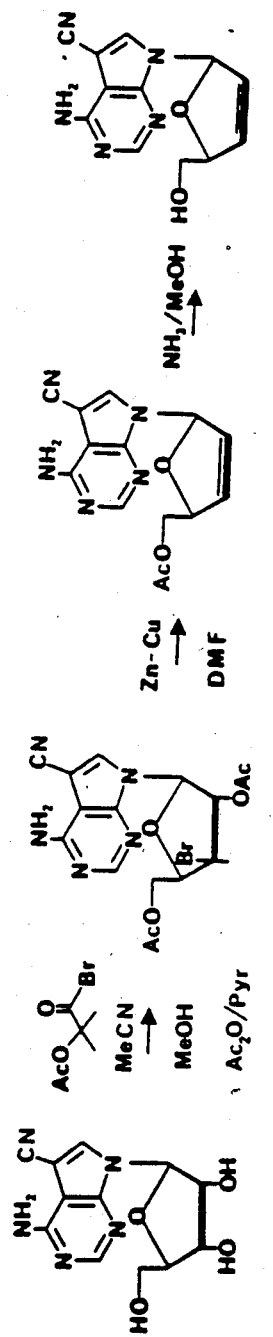
FIGURE II

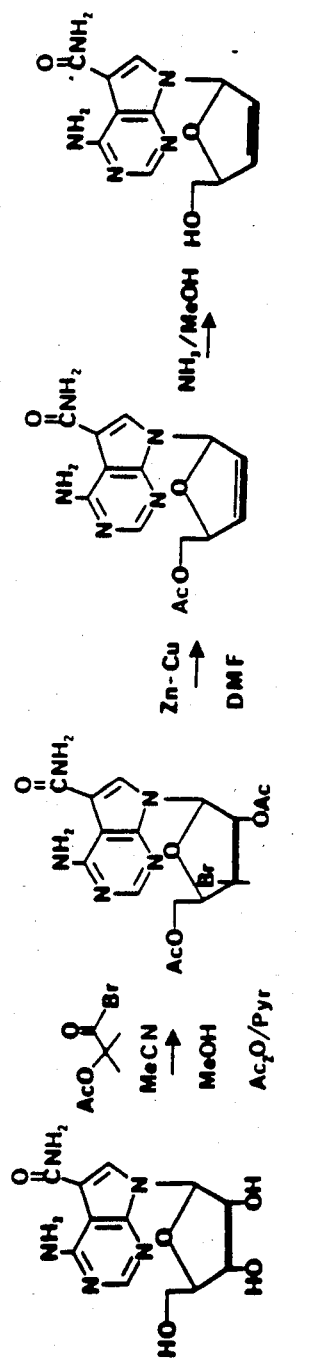
FIGURE III

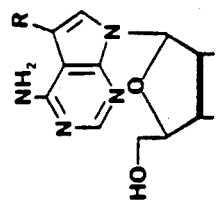
| | | |
|---|---|---|
| 5 | R = | H |
| 10 | R = | CN |
| 15 | R = | CONH₂ |
H₂ ↑ Pd/C
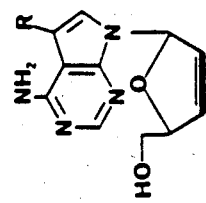
| | | |
|---|---|---|
| 4 | R = | H |
| 9 | R = | CN |
| 14 | R = | CONH₂ |
FIGURE IV

PYRROLO[2,3-D]PYRIMIDINE NUCLEOSIDES AS ANTIVIRAL AGENTS This invention was made with Government support under contracts numbered NO1AI42554 and NO-1AI72641 awarded by the National Institute of Allergy and Infectious Diseases. The Government has certain rights in this invention.

BACKGROUND OF THE INVENTION

The present invention relates to the use of purine nucleoside analogs in the treatment of viral infections. More particularly, the present invention relates to the use of certain substituted pyrrolo[2,3-d]pyrimidine nucleosides against human immunodeficiency virus (HIV-1), human cytomegalovirus (HCMV) and herpes simplex virus type 1 (HSV-1).

The antiviral activity of pyrrolo[2,3-d]pyrimidine nucleosides such as tubercidin, toyocamycin and sangivamycin and some substituted derivatives has been previously documented. Bergstrom, et al., "Antiviral Activity of C-5 Substituted Tubercidin Analogs," *J. Med. Chem.* (1984), Vol. 27, pp. 285–292; DeClercq, et al., "Antirhinovirus Activity of Purine Nucleoside Analogs," *Antimicrobial Agents and Chemotherapy* (1986), Vol. 29, No. 3, pp. 482–487. These compounds are particularly attractive as potential antiviral agents because of their stability to deamination by adenosine deaminase and glycosidic bond cleavage by purine nucleoside phosphorylases, the two major pathways of purine nucleoside inactivation.

However, although certain previously described pyrrolo[2,3-d] pyrimidine nucleosides have been reported as potently antiviral, their clinical usefulness is limited because they also exhibit unacceptable levels of cytotoxicity. It would thus be highly advantageous to find derivatives of these compounds which have decreased cytotoxicity but retain their antiviral activity, particularly against viruses which are currently of major concern such as the human immunodeficiency and herpes viruses.

The present invention relates to a class of substituted pyrrolo[2,3-d]pyrimidine nucleosides which exhibit antiviral activity, particularly against HIV-1, HCMV and HSV-1, and whose levels of cytotoxicity are significantly lower than their parent compounds.

SUMMARY OF THE INVENTION

The present invention relates to the treatment of viral infections, in particular those caused by human immunodeficiency virus type 1 (HIV-1) human cytomegalovirus (HCMV) and herpes simplex type 1 (HSV-1), with a therapeutically-effective amount of a compound selected from the group consisting of compounds of the following general formula, and pharmaceutically acceptable salts thereof:

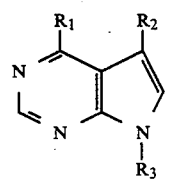

where $R_1$ is $NH_2$ or OH;

$R_2$ is H, CN,

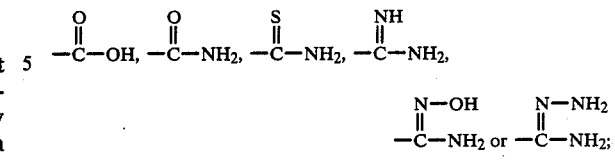

and
$R_3$ is 2,3-dideoxy-2,3-didehydroribofuranose or 2,3-dideoxyribofuranose.

BRIEF DESCRIPTION OF THE DRAWINGS

FIG. I illustrates a general scheme of synthesis of 2',3'-dideoxy-2',3'didehydrotubercidin (4) from the parent compound tubercidin (1).

FIG. II illustrates a general scheme of synthesis of 2',3'-dideoxy-2'3'-didehydrotoyocamycin (9) from the parent compound toyocamycin (6).

FIG. III illustrates a general scheme of synthesis of 2',3'-dideoxy-2',3'-didehydrosangivamycin (14) from the parent compound sangivamycin (II).

FIG. IV illustrates a general scheme of synthesis of the 2',3'-dideoxyribofuranosyl derivatives of the 2',3'-dideoxy-2',3'-didehydroribofuranosyl compounds of FIGS. I, II and III.

DESCRIPTION OF THE INVENTION

Chemical Structure of Compounds

The present invention relates to the use of pyrrolo [2,3-d]pyrimidine nucleosides in the treatment of viral infections, and, more specifically, to compounds of the following general formula and pharmaceutically acceptable salts thereof:

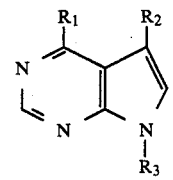

where
$R_1$ is $NH_2$ or OH;
$R_2$ is H, CN,

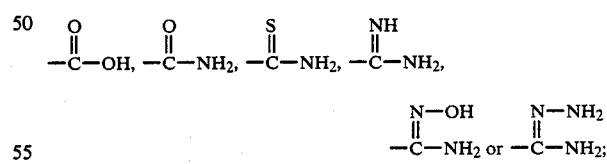

and
$R_3$ is 2',3'-dideoxy-2',3'-didehydroribofuranose or 2',3'-dideoxyribofuranose.

Preferred compounds of the invention include:
1. 4-amino-7-(2',3'-dideoxy-β-D-ribofuranosyl)pyrrolo[2,3-d]pyrimidine (2',3'-dideoxy-2',3'-didehydro tubercidin);
2. 4-amino-7-(2,3-dideoxy-β-D-ribofuranosyl)pyrrolo[2,3-d]pyrimidine (2',3'-dideoxytubercidin);
3. 4-amino-5-cyano-7-(2',3'-dideoxy-2',3'-didehydro-β-D-ribofuranosyl)-pyrrolo[2,3-d]pyrimidine (2',3'-dideoxy-2',3'-didehydrotoyocamycin);

4. 4-amino-5-cyano-7-(2',3'-dideoxy-β-D-ribofuranosyl) pyrrolo[2,3-d]pyrimidine (2',3'-dideoxytoyocamycin);
5. 4-amino-7-(2',3'-dideoxy-2',3'-didehydro-β-D-ribofuranosyl)pyrrolo-[2,3-d]pyrimidine-5-carboxamide (2',3'-dideoxy-2',3'-didehydrosangivamycin);
6. 4-amino-7-(2',3'-dideoxy-β-D-ribofuranosyl)pyrrolo[2,3-d]pyrimidine-5-carboxamide (2',3'-dideoxysangivamycin).

METHODS OF USE OF COMPOUNDS

The compounds of the present invention exhibit antiviral activity with acceptable levels of cytotoxicity and can thus be used in the treatment of viral infections. In particular, as shown in Table 1, these compounds are effective against human immunodeficiency virus type 1 (HIV-1), human cytomegalovirus (HCMV) and herpes simplex virus type 1 (HSV-1).

Additional viruses contemplated to be within the broad scope of treatment of the present invention include, but are not limited to, the following: Human B lymphotropic virus, Herpes simplex virus type 2, Varicella-zoster virus, Epstein-Barr virus, Necrotic rhinitis, Malignant catarrh, Allerton virus, Equine herpesvirus—1, Equine herpesvirus—2, Equine herpesvirus—3, Neurolymphomatosis, Influenza viruses, A, B and C, Parainfluenza viruses—1, 2, 3 and 4, Adenovirus, Rheovirus, Respiratory syncytial virus, Rhinoviruses, Coxsackie virus, Echo viruses, Epidemic gastroenteritis virus, Rubeola virus, Hepatitis A and B viruses, and Papovavirus.

The compounds of the present invention can be used in a therapeutically effective amount to treat viral infections in vivo in accordance with conventional procedures, for example, as an active ingredient in pharmaceutical compositions. The pharmaceutical compositions may take the form of tablets, lozenges, granules, capsules, pills, ampoules or suppositories. They may also take the form of ointments, gels, pastes, creams, sprays, lotions, suspensions, solutions and emulsions of the active ingredient in aqueous or nonaqueous diluents, syrups, granulates or powders. Moreover, pharmaceutical compositions containing a compound of the present invention, can also contain other pharmaceutically active compounds or a plurality of compounds of the invention to maximize their therapeutic effectiveness.

METHOD OF SYNTHESIS

The compounds of the present invention can be synthesized by the general procedure illustrated in FIGS. I-IV. Referring now to FIG. I, the parent pyrrolo[2,3-d]pyrimidine ribofuranosyl compound tubercidin (1) was dissolved in acetonitrile and reacted with 2-methyl-2-acetoxypropionyl bromide to introduce the bromine moiety in a trans orientation relative to the 2'-acetoxy moiety. The compound was then reacted with pyridine and acetic anhydride to acetylate any free hydroxyl moieties. The resultant intermediate compound (2) was then treated with zinc-copper couple and dimethylformamide to form a second intermediate compound (3), then with methanolic ammonia to yield 2'3'-dideoxy-2',3'-didehydrotubercidin (4).

A similar scheme of synthesis was followed with the parent compounds toyocamycin (6), as illustrated in FIG. II, and sangivamycin (11), as illustrated in FIG. III. As shown in FIGS. II and III, the only additional step in the synthesis of their 2',3'-dideoxy-2',3'-didehydro derivatives was the addition of methanol after reaction with the bromide compound to remove the 5'blocking moiety.

Referring now to FIG. IV, conversion of the 2'3'-dideoxy-2',3'-didehydroribofuranosyl compounds (4,9,14) of FIGS. I, II and III to their respective 2'3'-dideoxyribofuranosyl compounds (5,10,15) was achieved by hydrogenating in a Parr apparatus the 2',3'-dideoxy-2',3'-didehydro compound dissolved in alcohol with palladium on charcoal.

The specific procedure followed for the synthesis of each compound depicted in FIGS. I-IV is set out below in the specific examples.

SPECIFIC EXAMPLES

Chemical Synthesis

Example 1

Scheme I Compound 4

4-amino-7(2',3'-dideoxy-2',3'-didehydro-β-ribofuranosyl)-pyrrolo[2,3-d] pyrimidine (2',3'-dideoxy-2',3'-didehydrotubercidin)

2-Methyl-2-acetoxypropionyl bromide (7.07 g, 33.9 mmole) was added, with vigorous stirring to a suspension of finely ground tubercidin (3.0 g. 11.3 mmole) in acetonitrile (100 ml, dried over 3 Å sieves) and the mixture then stirred at room temperature for 1.5 hr. The resulting solution was partitioned between ice-cold 50% saturated sodium bicarbonate (300 mL) and ethyl acetate (300 mL). The organic layer was washed with brine (100 mL), dried over sodium sulphate, filtered, and the filtrate was evaporated to afford a crisp white foam (5.8 g). This foam was dissolved in pyridine (100 mL), 4-dimethylaminopyridine was added (40 mg, 0.4 mmole), and the solution was treated with acetic anhydride (4.0 mL, 43 mmole). The mixture was stirred at room temperature for 1 hr. and then evaporated to a thick oil. This oil was partitioned between ethyl acetate (300 mL) and water (300 ml). The organic layer was then washed with brine (100 ml), dried over sodium sulphate, filtered, and the filtrate evaporated to a yellow foam which was kept in vacuo for 72 hr. This foam was dissolved in dimethylformamide (150 ml) and treated with zinc-copper couple (20 g). The mixture was stirred for 1.5 hr. at 80°, then filtered through Celite. The Celite bed was washed with dimethylformamide (50 ml) and the combined filtrates were evaporated at 50°–60° to afford a syrup which was partitioned between ethyl acetate (100 ml) and water (300 ml). The water layer was then extracted with ethyl acetate (2×100 ml) and the combined organic fractions were washed with brine (200 ml), dried over magnesium sulphate, filtered and the filtrate was evaporated to a thick oil. This oil was further evaporated in vacuo to afford a soft foam. This foam was dissolved in methanol (35 ml), methanolic ammonia (35 ml, saturated at 0°) was added, and the solution was sealed in a pressure bottle and stirred at room temperature for 12 hr. The solution was evaporated to a thick oil and then further evaporated in vacuo at 50°–60° to afford a very thick oil. This oil was dissolved in chloroform (10 ml) and the solution was applied to a bed of silica (2 cm deep, 3 cm wide) slurry packed in a fritted disc funnel. This bed was eluted with solvent system A (300 ml). The first 100 ml of eluant was discarded, and the next 200 ml of eluant was collected and evaporated at 50°–60° to afford a thick oil. This oil was triturated with ether (5×20 ml), chloroform (15 ml) was added to the remaining residue and this mixture then heated at reflux. Ether was then slowly added (30 ml) and the mixture solidified upon cooling to room temperature. Additional ether was added (50 ml), the solid was collected by filtration and air dried to yield a tan solid (1.63 g). The mother liquor was combined with the ethereal extracts, the resulting solution was evaporated and then triturated with chloroform/ether (1:2, 30 ml) to afford an additional 0.4 g of solid. The solids were combined and suspended in boiling ethyl acetate (200 ml). Isopropanol (30 ml) was added, and the boiling mixture was stirred until all solid material had dissolved. Norit (200 mg) was added, and the mixture was filtered through Celite. The Celite bed was washed with ethyl acetate (20 ml). The combined filtrates were reduced in volume to approximately 50 ml by boiling. The solution was allowed to stand at room temperature for 4 hr. The solid was collected by filtration and air dried to afford 1.3 g of a tan solid. The material was further purified by dissolving 1.2 g in boiling ethanol (150 ml) and reducing the volume of the solution to 50 ml by boiling. The solution was allowed to cool to room temperature and then allowed to stand at 4° for 16 hr. The solid was collected by filtration to yield a solid (0.93 g), after drying at 80° under reduced pressure over phosphorous pentoxide. Some additional product (0.32 g) could be obtained by evaporating the ethyl acetate and ethanol mother liquors and crystallizing the resulting residue from ethanol (25 ml) for a total yield of 1.25 g (48%). mp 204°–205°; $^1$H NMR (DMSO-$d_6$): δ, 8.07 (s, 1H, H-2), 7.15 (d, 1H, H-6, $J_{(5,6)}$=3.71 Hz), 7.12 (bs, 1H, H-1'), 7.02 (bs, 2H, NH$_2$), 6.56 (d, 1H, H-5), 6.42 (ddd, 1H, H-3', $J_{(2',3')}$=6.01 Hz, $J_{(3',4')}$=$J_{(3',1')}$=1.62 Hz), 6.02 (ddd, 1H, H-2'), 4.96 (t, 1H, 5'-OH), 4.79 (m, 1H, H-4'), 3.50 (m, 2H, H-5' a,b); UV: $\lambda_{max}$ (nm) (log epsilon): MeOH, 271 (4.11); pH 1, 272 (4.04), 226 (4.36); pH 11, 271 (4.04), 224 (3.82); TLC: solvent A, $R_f$=0.21; Anal Calcd. for $C_{11}H_{12}N_4O_2$: C, 56.89: H, 5.20; N, 24.13. Found: C, 56.88; H, 5.22; N, 24.09.

Example 2

Scheme IV Compound 5
4-amino-7-(2',3'-dideoxy-β-D-ribofuranosyl)pyrrolo[2,3-d]-pyrimidine (2',3'-dideoxytubercidin)

A solution of compound 4 (0.5 g, 2.14 mmole) in absolute ethanol (75 ml), containing 10% palladium on charcoal (0.04 g) was hydrogenated for 7 hr. on a Parr hydrogenation apparatus at a pressure of 50 psi. The catalyst was removed by filtration through Celite. The Celite bed was washed with ethanol (10 ml) and the filtrates were evaporated to afford an oil. This oil was dissolved in chloroform (30 ml) and the solution was evaporated to afford a foam. After being kept in vacuo for 16 hr., this foam was dissolved in chloroform/methanol (6:1, v:v, 3 ml) and the solution was applied to a silica column (300 mm×22 mm). The column was eluted at a flowrate of 17 ml/min., with chloroform/methanol (6:1, v:v). The elution was followed by observing the absorbtion at 275 nm. The major fraction (eluting between 7.2 and 16.4 min.) was evaporated to dryness and kept in vacuo for 48 hr. to afford 380 mg of a crisp foam (75%): $^1$H NMR (DMSO-$d_6$): δ, 8.04 (s, 1H, H-2), 7.33 (d, 1H, H-6, $J_{(5,6)}$=3.6 Hz), 6.99 (bs, 2H NH$_2$), 6.55 (d, 1H, H-5), 6.33 (dd, 1H, H-1' $J_{(1',2'a)}$=$J_{(1',2'b)}$=6.8 Hz), 4.99 (bs, 1H, 5'-OH), 4.03 (m, 1H, H-4'), 3.55 and 3.46 (2m, 2H, H-3'ab); UV $\lambda_{max}$(nm) (log epsilon): MeOH, 273 (3.99), 228 (4.35); pH 1, 273 (4.02), 277 (4.35); pH 11, 271 (4.07), 225 (3.95); TLC; solvent A, $R_f$=0.24: Anal. Calcd. for $C_{11}H_{14}N_4O_2$ (¼ H$_2$O): C, 55.34; H, 6.12; N, 23.47. Found: C, 55.25; H, 6.29; N, 23.27.

Example 3

Scheme II Compound 9
4-amino-5-cyano-7-(2',3'-dideoxy-2',3'-didehydro-β-D-glycero-pentofuranosyl)-pyrrolo[2,3-d]pyrimidine (2',3'-dideoxy-2',3'-didehydrotoyocamycin)

A vigorously stirred suspension of finely ground toyocamycin (5.8 g, 20 mmole) in acetonitrile (125 ml, dried over 3 Å was chilled with an ice bath to ca. 5°. To this suspension was added 2-methyl-2-acetoxypropionyl bromide (11.7 g, 56 mmol) over a 5 min. period via a syringe, with continuous stirring and cooling. After the addition was complete, the ice bath was removed and stirring was continued for an additional 1 hr. After this time, TLC analysis of the mixture revealed two bands ($R_f$=0.60, 0.30; solvent system A; plate exposed to conc. ammonia vapor for ca 1 sec before developing). The solution was then treated with methanol (5 ml) and stirring was continued for an additional 15 min. After this time, TLC analysis showed an absence of the faster running band. The solution was then evaporated to afford a sticky foam which was kept in vacuo for 0.5 hr. and then dissolved in pyridine (150 ml). Acetic anhydride (12 ml, 127 mmole) was then added to this solution and stirring was continued for an additional 0.5 hr. At this time, TLC showed one major band ($R_f$=0.6). The solution was then evaporated in vacuo to a thick oil which was partitioned between ethyl acetate (300 ml) and water (600 ml). The organic layer was washed with water (2×600 ml) and brine (300 ml), dried over magnesium sulphate, filtered, and evaporated to a foam which was treated with methanol (100 ml) and again evaporated to a foam which was then kept in vacuo for 0.5 hr. This foam was dissolved in hot methanol (125 ml) and the solution was allowed to cool to room temperature. The solution was allowed to stand at room temperature for 2 hr. then kept at ca. 5° for 1 hr. The crystalline product was collected by filtration, washed with cold methanol (30 ml) and dried at 80° under reduced pressure over phosphorous pentoxide for 16 hr. to afford 4.2 g of a white solid. Additional material could be obtained by evaporating the mother liquor, triturating the residue with hot ligroin (3×75 ml), co-evaporating the residue with methanol (2×50 ml), and finally crystallizing the resulting foam from hot methanol (30 ml). Drying the solid as above, yielded 1.2 g of a hard glass which was identical by TLC ($R_f$=0.6, solvent system A) to the first crop.

To a solution of the material obtained as described above (7.5 g, 17 mmole), in dimethylformamide (25 ml), was added acetic acid (0.25 ml, 2.6 mmole) and zinc-copper couple (7.5 g). After stirring for 10 min., the mixture became warm and TLC analysis (solvent system A) shows the absence of starting material ($R_f$=0.63, chars yellow) and the presence of a new spot ($R_f$=0.57, chars blue). The mixture was treated with water (10 ml) and filtered through Celite. The Celite bed was washed with dimethylformamide (20 ml) and the combined filtrates diluted to a volume of 200 ml wth water. This solution was extracted with ethyl acetate (5×40 ml) and the combined extracts were washed with water (40 ml) and then brine (3×40 ml). The organic layer was then dried over magnesium sulphate, filtered, and evaporated to afford a sticky foam which was co-evaporated with methanol (2×40 ml). This foam was then dissolved in hot methanol (20 ml), filtered, and allowed to crystallize for 2 hr. at room temperature. The product was collected by filtration, and dried as described above to afford 2.7 g (52%) of the 5'-O- acetate of the title compound: mp 148°–149°; $^1$H NMR (DMSO-d$_6$): δ8.25 (s, 1H, H-2), 8.09 (s, 1H, H-6), 7.13 (bs, H, H-1'), 6.88 (bs, 2H, NH$_2$), 6.51 (d, 1H, H-3', J$_{(2',3')}$=6 Hz), 6.17 (d, 1H, H-2'), 5.06 (bs, 1H, H-4'), 4.16 (m, 2H, H-5'ab), 2.01 (s, 3H, 5'CH$_3$CO).

A suspension of the 5'-O-acetate (2.0 g 6.3 mmole) in methanolic ammonia (75 ml, saturated at 0°) was sealed in a pressure bottle and stirred at room temperature for 6 hr. The resulting yellow solution was reduced in volume by boiling on a steam bath to approximately 20 ml. The solution was then allowed to crystallize at room temperature. The solid was collected by filtration, washed with methanol (5 ml) and air dried to afford 1.2 g of a white solid (22% overall from toyocamycin). A sample (1.0 g) of this material was recrystallized by dissolving it in methanol (40 ml), diluting the solution with water to a final volume of 100 ml, and allowing the solution to stand overnight at room temperature. The solid was collected by filtration and washed with water (10 ml) to yield 0.56 g of material after air drying. A sample of this material (0.2 g) was dissolved in solvent system A (10 ml) and the solution was chromatographed on a silica column (22 mm×300 mm) using solvent system A at a flowrate of 17 ml/min. The elusion was followed by observing the absorbtion at 280 nm. The desired fraction (eluting between 4.2 and 10.0 min.) was immediately evaporated under water aspirator pressure at room temperature. The residue was suspended in methanol (5 ml) and filtered. The product cake was washed with methanol (5 ml) and ether (5 ml) to afford 0.12 g of a white powder, after air drying: mp 201°–202°; $^1$H NMR (DMSO-d$_6$): δ, 8.25 (s, 1H, H-2), 8.22 (s, 1H, H-6), 7.13 (bs, 1H, H-1'), 6.87 (bs, 2H, NH$_2$), 6.48 (d, 1H, H-3'.J$_{(2',3')}$=6.05 Hz), 6.07 (d, 1H, H-2'), 5.00 (t, 1H, 5'-OH), 4.87 (m, 1H, H-4'), 3.58 (m, 2H, H-5'ab); UV λ$_{max}$(nm) (log epsilon): [MeOH, 279 (4.31), 229 (4.17); pH 1, 273 (4.26), 233 (4.39); pH 11, 278 (4.33), 231 (4.20);] TLC: Solvent system A, R$_f$=0.38; IR(KBr) 2220 cm$^{-1}$ (cyano); Anal. Calcd. for C$_{12}$H$_{11}$N$_5$O$_2$: C, 56.03; H, 4.31: N, 27.23. Found: C, 56.08; H, 4.36; N, 27.16.

Example 4

Scheme IV Compound 10

4-amino-5-cyano-7-(2',3'-dideoxy-β-D-ribofuranosyl)-pyrrolo-[2,3-d]-pyrimidine (2', 3'-dideoxytoyocamycin)

A solution of compound 9 (0.4 g, 1.7 mmole) in ethanol/water (90:10, v:v, 30 ml) containing 5% palladium on charcoal (0.05 g) was hydrogenated on a Parr apparatus for 1 hr. at a pressure of 50 psi. An additional portion (0.1 g) of the catalyst was then added, and the hydrogenation was continued for an additional 2 hr. The catalyst was removed by filtration through Celite, and the Celite bed was then washed with ethanol (20 ml). The combined filtrates were evaporated under aspirator pressure at 45°–50°, and the residue was co-evaporated with ethanol (2×20 ml). The residue was crystallized from isopropanol (20 ml), and washed with ether (20 ml) to yield 0.23 g (57%) of a white solid, after air drying. A sample (0.1 g) of this material was dissolved in DMSO (2 ml) and the solution was chromatographed in two portions on a C-18 column (22 mm×250 mm, 50 mm guard column) using water/methanol (70:30, v:v) at a flowrate of 12 ml/min. The elution was monitored by observing the absorbtion at 280 nm. The desired fraction eluted between 23 and 42 min. This fraction was combined with the corresponding fraction from a duplicate run and evaporated under water aspirator pressure at 35° to a volume of 8 ml. The resulting suspension was heated to dissolve the solids and the solution was then allowed to stand at room temperature for 3 hr. The resulting solid was collected by filtration, washed with water (10 ml) and air dried to afford 0.053 g of a white solid: mp 197°–197.5°; $^1$H NMR (DMSO-d$_6$): δ8.44 (s, 1H, H-2), 8.20 (s, 1H, H-6), 6.83 (bs, 2H, NH$_2$), 6.36 (dd, 1H, H-1', J=3.13, 6.84 Hz), 5.02 (t, 1H, 5'-OH), 4.08(m, 1H, H-4'), 3.62 and 3.54 (2m, 2H, H-5'ab), 2.41 and 2.22 (2m, 2H, H-2'ab), 1.97 (m, 2H, H-3'ab); UV λ$_{max}$(nm) (log epsilon): MeOH, 280 (4.05), 231 (3.93); pH 1, 274 (3.92), 235 (4.08); pH 11, 279 (4.03), 234 (3.89); TLC; solvent system A, R$_f$=0.40, chars yellow; IR(KBr) 2220 cm$^{-1}$ (cyano); Anal. Calcd. for C$_{12}$H$_{13}$N$_5$O$_2$: C, 55.59; H, 5.05; N, 27.02. Found: C, 55.68; H, 5.08; N, 26.91.

Example 5

Scheme III Compound 14

4-amino-7-(2',3'-dideoxy-2',3'-didehydro-β-D-ribofuranosyl)-pyrrolo-[2,3-d]pyrimidine-5-carboxamide (2',3'-dideoxy-2',3-didehydrosang-ivamycin)

A rapidly stirred suspension of sangivamycin (6.18 g, 20 mmole) in acetonitrile (125 ml, dried over 3 Å sieves) was treated with 2-methyl-2-acetoxypropionyl bromide (10.4 g, 50 mmole) and the stirring was continued for 1.5 hr. An additional portion of the bromo compound was added (1 g, 5 mmole) and stirring was continued for another 5 min. Methanol was then added (5 ml) and the mixture was stirred for 10 min. The solvent was removed by evaporation. Pyridine (100 ml) and acetic anhydride (10 ml 0.1 mmole) were added to the residue and the mixture was shaken vigorously for 5 min. in order to cause dissolution of the gummy residue. After an additional 15 min. of stirring, TLC analysis of the mixture shows one major product (R$_f$=0.51, solvent system A). The solution was evaporated, and the resulting gummy residue was treated with ethanol/water (1:1, v:v, 100 ml) and the solution was once again evaporated to afford a gummy residue. This gum was treated with isopropanol (200 ml) and the mixture was heated to reflux temperature. The mixture was allowed to cool to room temperature, the solid was collected by filtration (6.8 g) and combined with the solid obtained (1.2 g) by concentration of the mother liquor and trituration of the residue with isopropanol (100 ml). A sample (7.5 g) of this material was dissolved in hot isopropanol/methanol (4:2, v:v, 600 ml) and the volume of the solution was reduced to 300 ml by boiling on a hot plate. The solid, which had precipitated on cooling to room temperature, was collected by filtration, washed with isopropanol (20 ml) and ether (50 ml) to afford 5.2 g of a white powder. This powder (4.0 g) was dissolved in dimethylformamide (70 ml) and the solution was treated with zinc-copper couple (1.5 g). After stirring for 2 hr., TLC (solvent system A) shows the absence of starting material (R$_f$=0.51 and the presence of product (R$_f$=0.31). The spent zinc-copper couple was removed by filtration through Celite, and the Celite bed was washed with dimethylformamide (3×15 ml). The combined filtrates were evaporated to afford an oil which solidified upon treatment with ethanol (50 ml). The solid was collected by filtration and washed with ethanol (10 ml) to afford 3.1 g of the crude acetate of the title compound.

A suspension of the acetate (2.0 g) in methanolic ammonia (40 ml, saturated at 0°) was stirred at room temperature in a pressure bottle for 24 hr. and then kept at −20° for 24 hr. The solid was removed by filtration and washed with methanol (5 ml) and ether (10 ml). The combined filtrates were evaporated to dryness and the residue was triturated with hot ethanol (30 ml). The solid material was collected by filtration, after cooling the suspension to room temperature, washed with ethanol (10 ml) and ether (10 ml) to afford 0.76 g of the crude title compound (29% overall from sangivamycin). A sample (0.5 g) of this material was dissolved in water (10 ml) and the solution was applied to a Sephadex LH-20 column (2.5 cm×20 cm). The column was eluted with water while the elution was monitored by TLC (solvent system A). The first product containing fraction ($R_f=0.14$, 10 ml) was discarded with the next 100 ml of eluent being collected and then evaporated to dryness. The residue was triturated with ethanol (20 ml), the solid was collected by filtration, washed with ethanol (5 ml) and ether (10 ml) to afford 0.29 g of a white powder, after air drying. A sample (0.1 g) of this material was dissolved in chloroform/methanol/water (80:10:2, v:v:v, 3 ml) and the solution was chromatographed on a silica column (20 mm×100 mm, 10 micron silica) using chloroform/methanol (8:1, v:v) at a flowrate of 15 ml/min. The elution was followed by observing the absorbtion at 280 nm and the fraction containing the product (eluting between 4 and 12 min.) was collected and evaporated. The residue was triturated with methanol (3 ml) and the solid was collected by filtration, washed with methanol (2 ml) and ether (5 ml) to afford 0.068 g of a white solid, mp 240° dec., $^1$H NMR (DMSO-d$_6$): δ, 8.10 (2, 1H, H-2), 8.00 and 7.32 (2bs, 2H, NH$_2$), 7.95 (s, 1H, H-6), 7.15 (bs, 1H, H-1'), 6.54 (d, 1H, H-3',J$_{(2',3')}$=5.98 Hz), 6.08 (d, 1H, H-2'), 4.92 (t, 1H, 5'-OH), 4.81 (bs, 1H, H-4'), 3.53 (m, 2H H-5'ab); UV λ$_{max}$(nm) (log epsilon): MeOH, 281 (4.12), 230 (3.97); pH 1,275 (4.02), 226 (4.10); pH 11, 280 (4.08), 233 (3.87); TLC: solvent system A, R$_f$=0.14; Anal. Calcd. for C$_{12}$H$_{13}$N$_5$O$_3$: C, 52.36; H, 4.76; N, 25.44. Found: C, 52.16; H, 4.57; N, 25.28.

Example 6

Scheme IV Compound 15

4-amino-7-(2',3'-dideoxy-β-D-ribofuranosyl)pyrrolo[2,3-d]-pyrimidine-5-carboxamide (2',3'-dideoxysangivamycin)

A suspension of compound 14 (0.15 g, 0.54 mmol) in methanol (50 ml) containing 5% palladium on charcoal (0.05 g) was hydrogenated on a Parr apparatus for 8 hr. at 35 psi. The catalyst was removed by filtration through Celite and the Celite bed was washed with methanol (2×10 ml). The combined filtrates were evaporated to a thick oil which was then co-evaporated with ethanol (2×10 ml) and isopropanol (10 ml). The resulting foam was then treated with ether (30 ml), and the resulting solid was collected by filtration, washed with ether (10 ml) and air dried to afford 0.12 g of a white solid. A sample (0.09 g) was dissolved in chloroform/methanol (8:1, v:v, 5 ml) and the solution was chromatographed on a silica column (20 mm×100 mm, 10 micron silica) using chloroform/methanol (8:1, v:v) at a flowrate of 15 ml/min. The elution was monitored by observing the absorbtion at 280 nm and the fraction eluting between 5 min. and 10 min. was collected and evaporated. The residue was triturated with methanol (3 ml). The solid was collected by filtration, washed with methanol (3 ml) and ether (5 ml), then allowed to air dry to afford 0.071 g of a white solid (47%): mp 207°–208°. $^1$H NMR (DMSO-d$_6$): δ, 8.08 (s, 1H, H-2), 8.05 (s, 1H, H-6), 7.94, 7.32 (2bs, 2H, NH$_2$), 6.38 (q, 1H, H-1'), 4.86 (t, 1H, 5'-OH); 4.06 (q, 1H, H-4'), 3.54 (m, 2H, H-5'ab), 262 (m, 1H H-2'ab), 2.20 9m, 1H, H-2'b), 2.05 (m, 2H, H-3'ab); UV λ$_{max}$(nm) (log epsilon): MeOH, 282 (4.08); pH 1, 232 (4.15), 276 (4.09); pH 11, 236 (3.93), 245 (3.89), 281 (4.13); TLC: Solvent system A R$_f$=0.14; Anal. Calcd. for C$_{12}$H$_{15}$N$_5$O$_3$ ¼ H$_2$O: C, 51.15; H, 5.54; N, 24.86. Found: C, 51.43; H, 5.50; N, 24.67.

Testing

The following procedures were followed to test the compounds of the specific examples:

A.

Assays with Herpes Virus Type 1 (HSV-1) and Human Cytomegalovirus (HCMV)

1. Cell Lines and Viruses

KB cells, an established human cell line derived from an epidermoid oral carcinoma, were routinely grown in minimal essential medium (MEM) with Hanks salts [MEM(H)] supplemented with 5% fetal bovine serum. African green monkey kidney (BSC-1) cells and diploid human foreskin fibroblasts (HFF cells) were grown in MEM with Earle's salts [MEM(E)] supplemented with 10% fetal bovine serum. Cells were passaged according to conventional procedures as described in Shipman, C., Jr.; Smith, S. H.; Carlson, R. H.; Drach, J. C. *Antimicrob. Agents Chemother.*, 1976, 9, 120. The plaque-purified isolate, P$_O$, of the Towne strain of HCMV was used in all experiments and was a gift of Dr. Mark Stinski, University of Iowa. The S-148 strain of HSV-1 was provided by Dr. T. W. Schafer of Schering Corp. Stock preparations of HCMV and HSV-1 were prepared and titered as described in Turk, S. R.; Shipman, C., Jr.; Nassari, R.; Genzlinger, G.; Krawczyk, S. H.; Townsend, L. B.; Drach, J. C. *Antimicrob. Agents Chemother.*, 1987, 31, 544.

2. Assays for antiviral activity

HCMV plaque reduction experiments were performed using monolayer cultures of HFF cells by a procedure similar to that referenced above for titration of HCMV, with the exceptions that the virus inoculum (0.2 ml) contained approximately 50 PFU of HCMV and the compounds to be assayed were dissolved in the overlay medium. HSV-1 plaque reduction experiments were performed using monolayer cultures of BSC-1 cells. The assay was performed exactly as referenced above for HSV-1 titration assays except that the 0.2 ml of virus suspension contained approximately 100 PFU of HSV-1 and the compounds to be tested were dissolved in the overlay medium.

3. Cell cytotoxicity assays

Two basic tests for cellular cytotoxicity were routinely employed for compounds examined in antiviral assays. Cytotoxicity produced in HFF and BSC-1 cells was estimated by visual scoring of cells not affected by virus infection in the plaque reduction assays described above. Cytopathology was estimated at 35- and 60-fold magnification and scored on a zero to four plus basis on the day of staining for plaque enumeration. Cytotoxicity in KB cells was determined by measuring the effects of compounds on the incorporation of radioactive precursors into DNA, RNA and protein as described in Turk, S. R.; Shipman, C., Jr.; Nassari, R.; Genzlinger, G.; Krawczyk, S. H.; Townsend, L. B.; Drach, J. C. *Antimicrob. Agents Chemother.*, 1987, 31, 544.

B.
Assays with Human Immunodeficiency Virus Type 1 (HIV-1)

1. Cell Lines and Virus

The human OKT4+T-cell clone, ATH8, was obtained from Dr. Samuel Broder's laboratory (NCI) through Dr. Hiroaki Mitsuya. These cells are propagated in RPMI 1640 medium supplemented with 4 mM glutamine, 15% heat-inactivated fetal bovine serum, antibiotics (50 units of penicillin and 50 μg of streptomycin per ml), and 50 units of recombinant-derived human interleukin-2 (ala-125; AMGen Biologicals) per ml. The clone H9 cell lines, an OKT4+human T-cell line which is permissive for HIV replication but largely resistant to virus-induced CPE, H9 cells productively infected with the HTLV-III$_B$ strain of HIV, and H9 cells productively infected with the RF-II Haitian variant of HIV have been obtained from Dr. Robert Gallo's laboratory (NCI) through Dr. Howard Streicher. These cell lines are propagated in RPMI 1640 medium supplemented with 4 mM glutamine, 20% heat-inactivated fetal bovine serum, and antibiotics (50 units of penicillin and 50 g of streptomycin per ml). For infectious virus, undiluted culture supernate from Ho/HTLV-III$_B$ producer cells is used.

2. CPE-Inhibition Assay in ATH8 Cells

The testing of compounds for antiviral activity employed the modified CPE-inhibition assay described in Mitsuya, H.; Weinhold, K. J.; Furman, P. A.; St. Clair, M. H.; Lehrman, S. N.; Gallo, R. C.; Bolognesi, D.; Barry, D. W.; Broder, S. *Proc. Natl. Acad. Sci. USA*, (1985) 82, 7096 and Mitsuya, H.; Broder, S. *Proc. Natl. Acad. Sci. USA*, 1986, 83 1911. The assay is based on the ability of uninfected AHT8 cells to grow and form a pellet at the bottom of a culture tube. Starting about 4 days after HIV addition, infected ATH8 cells begin to die and the pellet starts to break up. The cell pellet is completely destroyed within 10 days. The protective effect of test compounds was assessed by adding them at varying concentrations to the cultured cells at the time of virus infection, then monitoring the status of the cell pellet.

ATH8 cells were used as the primary targeted cells in the HIV-induced CPE-inhibition assay. Cells were treated with polybrene (2 μg/ml in growth medium) for 30 minutes at 37° C., then collected by gentle centrifugation (40×g for 15 minutes at room temperature) and resuspended in clarified (8000×g for 15 minutes at 4° C.) supernate freshly harvested from 48 hour post-passage H9HTLV-III$_B$ cells. Following a 60 minute absorption period at 37° C., the cells were dispensed into the U-bottom wells of 96-well trays (2×10$^4$ cells in 0.1 ml per well). An equal volume (0.1 ml) of supplemented ROMI 1640 medium containing test compound and twice the normal concentration of interleukin-2 were added to each well. These compounds were evaluated at seven half-log dilutions. Triplicate virus-infected cultures and one uninfected compound cytotoxicity control culture were included at each dosage level. Cultures were incubated at 37° C. in a humidified atmosphere of 5% $CO_2$ in air. On day 10 post-infection aliquots were taken from individual wells and the total cell number and cell viability (based on trypan-blue dye exclusion) determined. Dideoxycytidine was assayed in parallel as a positive control.

C.
Data Analysis

Dose-response relationships were constructed by linearly regressing the percent inhibition of parameters derived in the preceding sections against log drug concentrations. 50% inhibitory (I$_{50}$) concentrations were calculated from the regression lines. The three I$_{50}$ concentrations for inhibition of DNA, RNA and protein synthesis were averaged to give the values reported in Table I for KB cell cytotoxicity. Samples containing positive controls (acyclovir, ganciclovir, or vidarabine) were used in all assays. Results from sets of assays were rejected if inhibition by the positive control deviated from its mean response by more than 1.5 standard deviations.

TABLE 1

Antiviral Activity and Cytotoxicity of 4,5-Substituted 7-(β-D-Pentofuranosyl) Pyrrolo[2,3-d]pyrimidines.

| | | 50% Inhibitory Concentration (μM) | | | | | | |
|---|---|---|---|---|---|---|---|---|
| | | Virus Tested | | | Cytotoxicity | | | |
| Compound | No. | HIV | HCMV | HSV-1[a] | ATH8 | HFF[b] | BSC[b] | KB[c] |
| Dideoxytubercidin | 5 | — | >100 | >100 | — | >100 | >100 | — |
| Dideoxydidehydrotubercidin | 4 | — | >100 | >100 | — | >100 | >100 | — |
| Dideoxytoyocamycin | 14 | 3 | 18 | 21 | 100 | >100 | >100 | 54 |
| Dideoxydidehydrotoyocamycin | 9 | — | 5.1 | 41 | — | >100 | >100 | >100 |
| Dideosysangivamycin | 15 | 3 | >100 | >100 | 100 | >100 | >100 | >100 |
| Dideoxydidehydrosangivamycin | 13 | — | >100 | >100 | — | >100 | >100 | 54 |

[a]In experiments with HSV-1 both the HF and 148 strains were used.
[b]Visual cytotoxicity scored on uninfected HFF or BSC cells at time of HCMV or HSV-1 plaque determination.
[c]Average percent inhibition of DNA, RNA and protein synthesis determined in KB cells as described in the text.

What is claimed is:

1. The method of treating human cells infected with a virus selected from the group consisting of herpes virus and cytomegalovirus, said method comprising the step of contacting said cells with a composition comprising a therapeutically effective amount of a compound selected from the group consisting of a compound of the following formula and pharmaceutically acceptable salts thereof:

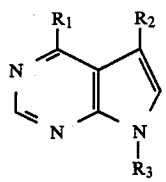

where
R₁ is NH² or OH;
R₂ is H, CN,

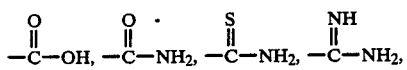

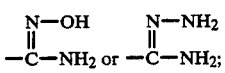

and
R₃ is 2',3'-dideoxy-2',3'-didehydro-β-D-ribofuranose or 2',3'-dideoxyribofuranose.

2. The method of claim 1 wherein R₁ is NH₂, R₂ is H and R₃ is 2',3'-dideoxy-2',3'-didehydroribofuranose.

3. The method of claim 1 wherein R₁ is NH₂, R₂ is H and R₃ is 2',3'-dideoxyribofuranose.

4. The method of claim 1 wherein R₁ is NH₂, R₂ is CN and R₃ is 2',3'-dideoxy-2',3'-didehydroribofuranose.

5. The method of claim 1 where R₁ is NH₂, R₂ is CN and R₃ is 2',3'-dideoxyribofuranose.

6. The method of claim 1 wherein R₁ is NH₂, R₂ is CONH₂ and R₃ is 2',3'-dideoxy-2',3'-didehydroribofuranose.

7. The method of claim 1 wherein R₁ is NH₂, R₂ is CONH₂ and R₃ is 2',3'-dideoxyribofuranose.

8. The method of claim 1 wherein the virus is human immunodeficiency virus type 1.

9. The method of claim 1 wherein the virus is herpes simplex virus type 1.

10. the method of claim 1 wherein the virus is human cytomegalovirus.

11. A compound selected from the group consisting of compounds of the following general formula and the pharmaceutically acceptable salts thereof:

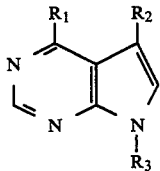

where
R₁ is NH² or OH;
R₂ is

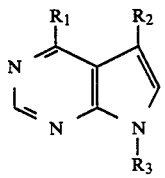

and

R₃ is 2',3'-dideoxy-2',3'-didehydroribofuranose; or 2',3'-dideoxyribofuranose.

12. The compound of claim 11 wherein R₁ is NH₂, R₂ is

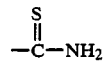

and R₃ is 2',3'-dideoxy-2',3'-didehydroribofuranose.

13. The compound of claim 11 wherein R₁ is NH₂, R₂ is

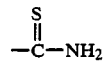

and R₃ is 2'3'-dideoxyribofuranose.

14. The compound of claim 12 wherein R₁ is NH₂, R₂ is CONH₂ and R₃ is 2',3'-dideoxy-2',3'-didehydroribofuranose.

15. The compound of claim 11 wherein R₁ is NH₂, R₂ is CONH₂ and R₃ is 2',3'-dideoxyribofuranose.

16. A treatment composition comprising an effective amount of a compound selected from the group consisting of compounds of the following general formula and pharmaceutically acceptable salts thereof:

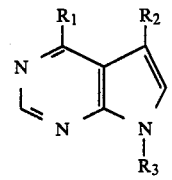

where R₁ is NH₂ or OH;
R₂ is H, CN

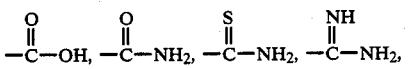

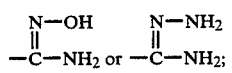

and
R₃ is 2',3'-dideoxy-2',3'-didehydroribofuranose or 2',3'-dideoxyribofuranose, and a pharmaceutically acceptable carrier where R₂ is not H or CN when R₁ is NH₂.

17. A compound selected from the group consisting of compounds of the following general formula and the pharmaceutically acceptable salts thereof:

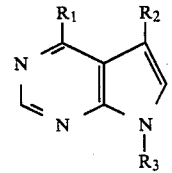

where R₁ is NH² or OH;
R₂ is H, CN, $-\overset{\overset{O}{\|}}{C}-OH$, $-\overset{\overset{O}{\|}}{C}-NH_2$, $-\overset{\overset{S}{\|}}{C}-NH_2$, $-\overset{\overset{NH}{\|}}{C}-NH-_2$, $-\overset{\overset{N-OH}{\|}}{C}-NH_2$ or $-\overset{\overset{N-NH_2}{\|}}{C}-NH_2'$; and $R_3$ is 2′,3′-dideoxy-2′,3′-didehydroribofuranose; or 2′,3′-dideoxyribofuranose, where $R_2$ is not H or CN when $R_1$ is $NH_2$.

* * * * *

UNITED STATES PATENT AND TRADEMARK OFFICE
CERTIFICATE OF CORRECTION

PATENT NO. : 4,892,865

DATED : January 9, 1990

INVENTOR(S) : Leroy B. Townsend et al.

It is certified that error appears in the above-identified patent and that said Letters Patent is hereby corrected as shown below: Title page:

all d's in [2,3-$\underline{d}$] should be italicized.

Other Publications: page 1, col. 2, line 23
"('-Deox-" should be -- (2'-Deox- --.

Other Publications: page 2, col. 2, line 13
"nucleosides 1, 211" should be --nucleosides[1,2]--.

UNITED STATES PATENT AND TRADEMARK OFFICE
CERTIFICATE OF CORRECTION

PATENT NO. :  4,892,865

DATED      :  January 9, 1990

INVENTOR(S) :  Leroy B. Townsend et al.

It is certified that error appears in the above-identified patent and that said Letters Patent is hereby corrected as shown below:

Column 2, line 11, "2,3-dideoxy-2,3-didehydroribofuranose or 2,3-" should be -- 2',3'-dideoxy-2',3'-didehydroribofuranose or 2',3'- --.

Column 2, line 61, after "dideoxy" insert -- 2',3'-didehydro- --.

Column 2, line 64, "2,3-dideoxy" should be -- 2',3'-dideoxy --.

Column 5, line 68, "0.24:" should be --0.24;--.

Column 6, line 61, "wth" should be --with--.

UNITED STATES PATENT AND TRADEMARK OFFICE
CERTIFICATE OF CORRECTION

PATENT NO. : 4,892,865            Page 3 of 3

DATED : January 9, 1990

INVENTOR(S) : Leroy B. Townsend et al.

It is certified that error appears in the above-identified patent and that said Letters Patent is hereby corrected as shown below:

Column 8, line 27, "2',3-didehydrosang-ivamycin" should be --2',3'-didehydrosangivamycin--.

Column 10, line 8, "9m," should be -- (9m, --.

Column 13, lines 58-65, "$R_2$ is

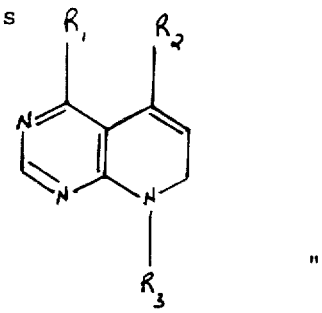

should be

-- $R_2$ is $-\overset{O}{\underset{\|}{C}}-OH$, $-\overset{O}{\underset{\|}{C}}-NH_2$, $-\overset{S}{\underset{\|}{C}}-NH_2$, $-\overset{NH}{\underset{\|}{C}}-NH_2$, $-\overset{N-OH}{\underset{\|}{C}}-NH_2$, or $-\overset{N-NH_2}{\underset{\|}{C}}-NH_2$ --.

Column 14, line 19, "claim 12" should be --claim 11--.

Signed and Sealed this

Twelfth Day of January, 1993

Attest:

DOUGLAS B. COMER

Attesting Officer        Acting Commissioner of Patents and Trademarks